US010626426B2

(12) United States Patent
Bae et al.

(10) Patent No.: US 10,626,426 B2
(45) Date of Patent: Apr. 21, 2020

(54) MICROORGANISM OF GENUS *CORYNEBACTERIUM* HAVING AN ABILITY TO PRODUCE L-ARGININE AND A METHOD FOR PRODUCING L-ARGININE USING THE SAME

(71) Applicant: CJ CHEILJEDANG CORPORATION, Seoul (KR)

(72) Inventors: Hyun Ae Bae, Incheon (KR); Han Hyoung Lee, Seoul (KR); Min Gyeong Kang, Seoul (KR); Jong Hyun Kim, Gyeonggi-do (KR); Hye Won Kim, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/515,551

(22) PCT Filed: Oct. 13, 2015

(86) PCT No.: PCT/KR2015/010768

§ 371 (c)(1),
(2) Date: Mar. 29, 2017

(87) PCT Pub. No.: WO2016/060437

PCT Pub. Date: Apr. 21, 2016

(65) Prior Publication Data

US 2017/0226545 A1 Aug. 10, 2017

(30) Foreign Application Priority Data

Oct. 13, 2014 (KR) ........................ 10-2014-0137794
May 29, 2015 (KR) ........................ 10-2015-0076331

(51) Int. Cl.

| | |
|---|---|
| ***C12N 1/21*** | (2006.01) |
| ***C12P 13/10*** | (2006.01) |
| ***C12N 9/10*** | (2006.01) |
| ***C12N 1/20*** | (2006.01) |
| ***C12N 15/63*** | (2006.01) |
| ***C12R 1/15*** | (2006.01) |

(52) U.S. Cl.

CPC ................ *C12P 13/10* (2013.01); *C12N 1/20* (2013.01); *C12N 9/1018* (2013.01); *C12N 15/63* (2013.01); *C12R 1/15* (2013.01)

(58) Field of Classification Search

CPC ........... C12N 9/1003; C12Y 201/03003; C12P 13/10

See application file for complete search history.

(56) References Cited

U.S. PATENT DOCUMENTS 7,160,705 B2 1/2007 Suga et al.
7,252,978 B2 * 8/2007 Yamaguchi ............ C07K 14/34 435/106
2002/0045223 A1 4/2002 Suga et al.
2009/0123980 A1 5/2009 Ikeda et al.
2013/0344545 A1 12/2013 Choi et al.
2015/0147788 A1 * 5/2015 Lee ...................... C07K 14/245 435/108

FOREIGN PATENT DOCUMENTS

| | | | | |
|---|---|---|---|---|
| CN | 102021154 B | 9/2012 | | |
| JP | 63-079597 | 4/1988 | | |
| JP | 2010-515468 | 5/2010 | | |
| KR | 19900004425 B1 | 6/1990 | | |
| KR | 10-0620092 B1 | 8/2006 | | |
| KR | 10-0791659 B1 | 12/2007 | | |
| KR | 10-2008-0006799 A | 1/2008 | | |
| KR | 10-0830290 B1 | 5/2008 | | |
| KR | 10-0854234 B1 | 8/2008 | | |
| KR | 10-0930203 B1 | 11/2009 | | |
| KR | 10-1186128 B1 | 9/2012 | | |
| KR | 10-2012-0130580 A | 12/2012 | | |
| KR | 102013008212 A | * | 7/2013 | .............. C12N 1/21 |
| WO | WO 2008/007914 A1 | 1/2008 | | |
| WO | WO 2008/088148 A1 | 7/2008 | | |
| WO | WO 2008088149 A1 | 7/2008 | | |
| WO | WO-2008088149 A1 | * | 7/2008 | ........... C12N 9/1018 |

OTHER PUBLICATIONS

UniProt Database Accession No. Q8NRL4, Oct. 1, 2014, 1 page (Year: 2014).*
Zhou et al., Cell Mol. Life Sci. 63:2260-2290, 2006 (Year: 2006).*
Kozak, M., Gene 234:187-208, 1999 (Year: 1999).*
Yim et al., J. Ind. Microbiol. Biotechnol. 38:1911-1920, 2011 (Year: 2011).*
Database UniProt [online], Accession No. Q8NRL4, http//www.uniprot.orguniprotQ8NRL4, 5 pages, Jun. 2017.
Park et al., "Metabolic engineering of Corynebacterium glutamicum for L-arginine production," Nature Communications, vol. 5, Aug. 5, 2014 (Aug. 5, 2014), pp. 1-9.
Dou et al., "Improvement of I-Arginine Production by Overexpression of a Bifunctional Ornithine Acetyltransferase in Corynebacterium crenatum," Applied Biochemistry and Biotechnology 165(3): 845-855, Oct. 2011.
Sakanyan et al., "Genes and enzymes of the acetyl cycle of arginine biosynthesis in Corynebacterium glutamicum: enzyme evolution in the early steps of the arginine pathway," Microbiology 142: 99-108, 1996.
Ku et al., "Heterologous and homologous expression of the arginine biosynthetic argC~H cluster from Corynebacteriumcrenatum for improvement of I-arginine production," Journal of Industrial Microbiology & Biotechnology 39(3): 495-502, Mar. 2012.

(Continued)

*Primary Examiner* — David Steadman
(74) *Attorney, Agent, or Firm* — Cooley LLP

(57) ABSTRACT

The present invention relates to a microorganism of the genus *Corynebacterium* having an ability to produce L-arginine, and a method of producing L-arginine using the same.

3 Claims, No Drawings

Specification includes a Sequence Listing.

(56) References Cited

OTHER PUBLICATIONS

Xu et al., "Site-directed mutagenesis and feedback-resistant N-acetyl-L-glutamate kinase (NAGK) increase Corynebacterium crenatum L-arginine production," Amino Acids 43: 255-266, 2012.

* cited by examiner

MICROORGANISM OF GENUS *CORYNEBACTERIUM* HAVING AN ABILITY TO PRODUCE L-ARGININE AND A METHOD FOR PRODUCING L-ARGININE USING THE SAME

CROSS-REFERENCES TO RELATED APPLICATIONS

This application is a U.S. national phase application of International PCT Patent Application No. PCT/KR2015/010768, which was filed on Oct. 13, 2015, which claims priority to Korean Patent Application No. 10-2015-0076331, filed May 29, 2015 and Korean Patent Application No. 10-2014-0137794, filed Oct. 13, 2014. These applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_052_00US_ST25.txt. The text file is 32 KB, was created on Mar. 29, 2017, and is being submitted electronically via EFS-Web.

TECHNICAL FIELD

The present invention relates to a microorganism of the genus *Corynebacterium* having an ability to produce L-arginine and a method of producing L-arginine using the same.

BACKGROUND ART

L-arginine is an amino acid widely used in amino acid supplements, pharmaceutical drugs, foods, etc., and there has been demand for the development of efficient L-arginine production in the related industries.

The method of producing L-arginine by a conventional biological fermentation method is a method to produce L-arginine directly from carbon and nitrogen sources, and various methods including a method using an induced modified strain from a microorganism of the genus *Brevibacterium* or *Corynebacterium*, a method using a bacterial cell line developed to have enhanced amino acid-producing ability by cell fusion, etc., have been reported. Recently, a method of using a genetic recombinant strain, wherein a gene which inhibits the expression of arginine-biosynthesizing operon argR was inactivated (U.S. Pat. No. 7,160, 705), and a method of using the overexpression of argF in the arginine operon (Korean Patent No. 10-0854234), etc., were reported. In particular, the deletion in argR, which controls the arginine operon, has been considered as an important factor in arginine production.

According to the facts known so far, in a microorganism of *Corynebacterium*, argCJBDFR gene, which is involved in arginine biosynthesis, is constituted in the form of an operon and is subjected to feedback-inhibition by intracellular arginine (Vehary Sakanyan, et al., *Microbiology,* 142:9-108, 1996), thus imposing a limitation on its high-yield L-arginine production.

DISCLOSURE

Technical Problem

Accordingly, the present inventors, while endeavoring to increase the production yield of L-arginine, discovered that L-arginine can be produced in higher yield compared to the parental L-arginine-producing strain, by enhancing the activities of the arginine operon and ornithine carbamoyltransferase, without any deletion in arginine repressor (argR), which has conventionally been known as an important factor, thereby completing the present invention.

Technical Solution

An object of the present invention is to provide a microorganism of the genus *Corynebacterium* having an ability to produce L-arginine.

Another object of the present invention is to provide a method of producing L-arginine using the microorganism of the genus *Corynebacterium.*

Advantageous Effects

L-arginine can be produced in high yield using an L-arginine-producing microorganism of the genus *Corynebacterium* with enhanced activities of an arginine operon and ornithine carbamoyltransferase (ArgF or ArgF2) according to the present invention. Additionally, the L-arginine produced in high yield can be effectively used in human pharmaceutical and pharmacological industries.

BEST MODE

In an aspect to achieve the above-identified objects, the present invention provides a microorganism of the genus *Corynebacterium* capable of producing L-arginine with enhanced activities of an arginine operon and ornithine carbamoyltransferase.

In the present invention, the arginine operon is an operon consisting of enzymes involved in the mechanism of L-arginine biosynthesis, and in particular, arginine operon is consisted of enzymes constituting the cyclic steps of L-arginine biosynthesis. Specifically, the arginine operon consists of N-acetylglutamyl phosphate reductase (ArgC), glutamate N-acetyltransferase (ArgJ), N-acetylglutamate kinase (ArgB), acetylornithine aminotransferase (ArgD), ornithine carbamoyltransferase (ArgF), and arginine repressor (ArgR), and these enzymes are involved in the continuous enzyme reactions of L-arginine biosynthesis.

These enzymes that constitute the arginine operon are involved in the final L-arginine biosynthesis using L-glutamate as a precursor. The glutamate N-acetyltransferase (ArgJ) synthesizes N-acetylglutamate using L-glutamate as a precursor, and it may be one encoded by argJ gene. In particular, the acetyl group is obtained by decomposing N-acetylornithine into L-ornithine. It has been known that glutamate N-acetyltransferase is involved in a recycling reaction for L-arginine biosynthesis in microorganisms belonging to the genus *Corynebacterium.*

The produced N-acetylglutamate is synthesized into N-acetylglutamyl phosphate by N-acetylglutamate kinase (ArgB), ADP is produced by consuming ATP as a coenzyme, and may be one encoded by argB gene. Since it is known to be subjected to feedback inhibition by the final product, L-arginine, modifications releasing the feedback inhibition by L-arginine have been known, and there were reports that L-arginine productivity can be improved utilizing the same (Chinese Patent No. 102021154, and Amino Acids. 2012 July; 43(1): 255-66. doi: 10.1007/s00726-011-1069-x. Epub 2011 Sep. 8).

N-acetylglutamyl phosphate reductase (ArgC) is also called acetylglutamate semialdehyde dehydrogenase in *E.*

*coli* or yeasts, and may be encoded by argC gene. N-acetylglutamyl phosphate is converted into N-acetylglutamate 5-semialdehyde by this enzyme. NADPH is used as a coenzyme to supply energy. The produced N-acetylglutamate 5-semialdehyde is converted into N-acetylornithine using L-glutamate as an amino acid donor, and this reaction is mediated by acetylornithine aminotransferase (ArgD). Acetylornithine aminotransferase may be encoded by argD gene. The converted N-acetylornithine delivers its acetyl group to L-glutamate by the recycling reaction of glutamate N-acetyltransferase (ArgJ), and reacts as L-ornithine.

Ornithine carbamoyltransferase (ArgF) is generally called ornithine carbamoylase, and may be encoded by argF or argF2 genes. L-ornithine binds to carbamoyl phosphate to form L-citrulline, and a phosphate is produced as a side reaction product. The produced L-citrulline is finally synthesized into L-arginine by the enzyme reactions of argininosuccinic acid synthase (ArgG) and argininosuccinic acid lyase (ArgH), which are present separated from the arginine operon, mentioned above. L-arginine is synthesized by a total of 8 biosynthetic steps, and in the present invention, the enhancement of L-arginine productivity was induced by strengthening the activity of the arginine operon (argCJBDFR).

The enzymes that constitute the arginine operon may be included within the scope of the present invention as long as they have the activities described above, and specifically, the enzymes may be proteins derived from a microorganism of the genus *Corynebacterium*. More specifically, glutamate N-acetyltransferase (ArgJ) may include the amino acid sequence of SEQ ID NO: 19, or an amino acid sequence which has a homology to the sequence of at least 70%, specifically 80%, and more specifically 90% or higher. N-acetylglutamate kinase (ArgB) may include the amino acid sequence of SEQ ID NO: 21, or an amino acid sequence which has a homology of at least 70% to the sequence, specifically 80%, and more specifically 90% or higher. Additionally, in the case of the corresponding enzyme, modifications known in the art may be introduced in order to release feedback inhibition by arginine. N-acetylglutamyl phosphate reductase (ArgC) may include the amino acid sequence of SEQ ID NO: 23, or an amino acid sequence which has a homology of at least 70% to the sequence, specifically 80%, and more specifically 90% or higher. Acetylornithine aminotransferase (ArgD) may include the amino acid sequence of SEQ ID NO: 25, or an amino acid sequence which has a homology of at least 70% to the sequence, specifically 80%, and more specifically 90% or higher. Ornithine carbamoyltransferase (ArgF) may include an amino acid sequence of SEQ ID NO: 1 or SEQ ID NO: 3, or may include an amino acid sequence which has a homology of at least 70% to the amino acid sequence of SEQ ID NO: 1 or SEQ ID NO: 3. Specifically, ornithine carbamoyltransferase (ArgF) may include an amino acid sequence which has a homology of at least 75%, 80%, 85%, 90%, 95%, 96%, 97%, 98%, or 99% or higher to the amino acid sequence of SEQ ID NO: 1 or SEQ ID NO: 3. In addition, it is obvious that amino acid sequences including a deletion, modification, substitution or addition in one or more amino acid residues fall within the scope of the present invention, as long as they have the homology with the above proteins and have substantially the same or corresponding biological activity to the above proteins.

As used herein, the term "homology" refers to the degree of similarity between two amino acid sequences or nucleotide sequences for comparison, and their homology may be determined by comparing with the naked eye or using a bioinformatic algorithm, which provides analysis results of a degree of homology by aligning sequences for comparison. The homology between the two amino acid sequences may be indicated in percentages. The useful automated algorithms may be used in GAP, BESTFIT, FASTA, and TFASTA computer software modules of Wisconsin Genetics Software Package (Genetics Computer Group, Madison, Wis., USA). Other useful algorithms and homology determinations on alignment are already automated in software such as FASTP, BLAST, BLAST2, PSIBLAST, and CLUSTAL W.

In the present invention, the enhancement of the activity of the arginine operon may refer to the enhancement of the activity in at least one enzyme among the enzymes present in the arginine operon, however, it does not include the single enhancement of argR gene alone. For example, the enhancement of the arginine operon activity may refer to the enhancement of the activities of all enzymes present in the operon through the enhancement of the promoter for one enzyme present in the arginine operon, and specifically, may refer to the enhancement of the activity of the entire operon by the enhancement of the promoter for the N-acetylglutamyl phosphate reductase. Additionally, in the present invention, the increase in expression of a gene encoding at least one enzyme among the enzymes constituting the arginine operon may also be considered as the enhancement of the arginine operon activity.

As used herein, the term "enhancement" of activity refers to the provision of a microorganism without a particular activity of a protein with the activity of the protein, or increasing the intracellular activity in the microorganism possessing the activity of the protein, etc., and refers to the increasing of the intracellular activity of the protein compared to the intrinsic activity of the protein. As used herein, the term intrinsic activity refers to the active state of the enzyme possessed in the natural or pre-modified state by the microorganism belonging to the genus *Corynebacterium*.

For enhancing or increasing the activity of the enzyme, various methods known in the art may be applicable. Examples of the method, although they are not limited thereto, may include a method of increasing the copy number of nucleotide sequences encoding enzymes by further inserting a polynucleotide including a nucleotide sequence encoding the corresponding enzyme into a chromosome or introducing the polynucleotide into a vector system, etc., a method of replacing enzyme promoters with strong promoters, and specifically, may include a method of introducing a modification on the promoters, and a method of modifying the enzyme into one with strong activity by genetic modification.

Specific examples in the present invention may include a method of modifying the enzyme promoter present in the arginine operon to a promoter which is strong compared to the endogenous promoter, via modification or substitution of the promoter. An improved promoter or heterogeneous promoter with a nucleotide substitution modification may be connected instead of the promoter for the endogenous enzyme, and examples of the heterogeneous promoters may include pcj7 promoter (Korean Patent No. 10-0620092), lysCP1 promoter (Korean Patent No. 10-0930203), EF-Tu promoter, groEL promoter, aceA promoter, aceB promoter, etc., but are not limited thereto.

As used herein, the term "promoter" refers to a non-encoded nucleic acid sequence upstream of an encoding region, which includes a polymerase-binding region and has an activity of transcription initiation into mRNA of a gene downstream of the promoter, i.e., the DNA region where the polymerase binds and initiates the transcription of the gene, and is located on the 5' region of the mRNA transcription initiation region.

In the present invention, the enhancement of the ornithine carbamoyltransferase activity may be performed using various methods well known in the art, and they are the same as described above. Specifically, the enhancement may be achieved by transformation of an expression vector including a polynucleotide encoding the ornithine carbamoyltransferase into a bacterial strain, but is not limited thereto.

As used herein, the term "transformation" refers to an introduction of DNA into a host, thereby making the inserted DNA replicable as an extrachromosomal factor or by chromosomal integration. Specifically, the transformant of the present invention may be inserted into a chromosome via homologous recombination between the sequence of a nucleic acid molecule, which has the promoter activity within a vector after the transformation of the vector including the above DNA into a host cell, and the sequence in the promoter region of the endogenous target gene, or may be retained in the form of a plasmid.

The method of vector transformation of the present invention may include any method that can introduce a nucleic acid into a cell, and any appropriate standard technology known in the art may be selected and performed according to each host cell. For example, electroporation, calcium phosphate ($CaPO_4$) precipitation, calcium chloride ($CaCl_2$) precipitation, microinjection, a polyethylene glycol (PEG) method, a DEAE-dextran method, a cationic liposome method, a lithium acetate/DMSO method, etc., may be used, but the method is not limited thereto.

As used herein, the term "a microorganism of the genus *Corynebacterium* (*Corynebacterium* sp.)" may refer to all the strains belonging to the genus *Corynebacterium* having the L-arginine-producing ability, e.g., *Corynebacterium glutamicum, Corynebacterium ammoniagenes, Corynebacterium thermoaminogenes, Brevibacterium flavum, Brevibacterium fermentum*, etc., but is not limited thereto. Specifically, *Corynebacterium glutamicum* may be used, but the microorganism is not limited thereto.

In another aspect, the present invention provides a method for producing L-arginine including culturing an L-arginine-producing microorganism of the genus *Corynebacterium* in proper culture media.

In the present invention, the microorganism culture may be performed according to methods widely known in the art, and the conditions of culture temperature, culture hours, pH of culture medium, etc., may be appropriately adjusted. The known culture methods are described in detail in references (Chmiel; Bioprozesstechnik 1. Einfuhrung in die Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)). Additionally, culture methods may include batch culture, continuous culture, and fed-batch culture, and specifically, cultures may be performed continuously by a batch process or fed batch or repeated fed batch process, but are not limited thereto.

The culture media to be used should appropriately meet the required conditions of a particular strain. Culture media used for various microorganisms are already known (e.g., "Manual of Methods for General Bacteriology" from American Society for Bacteriology (Washington D.C., USA, 1981)). Carbon sources to be contained in the media may include saccharides and carbohydrates (e.g., glucose, sucrose, lactose, fructose, maltose, molasses, starch and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), organic acids (e.g., acetic acid), etc. These materials may be used individually or as a mixture, but are not limited thereto. Nitrogen sources to be contained in the media may include nitrogen-containing organic compounds (e.g., peptone, yeast extract, meat gravy, malt extract, corn steep liquor, soybean meal powder, and urea), and inorganic compounds (e.g., ammonium sulfate, ammonium chloride, ammonium phosphate, ammonium carbonate, and ammonium nitrate), and these materials may also be used individually or as a mixture, but are not limited thereto. Phosphorous sources to be contained in the media may include potassium dihydrogen phosphate or dipotassium hydrogen phosphate or an equivalent sodium-containing salt thereof, but are not limited thereto. Culture media may contain metal salts essential for growth (e.g., magnesium sulfate or iron sulfate), and essential growth-promoting materials such as amino acids and vitamins may be used, in addition to the materials described above. Additionally, an appropriate precursor may be further added to the culture media. The materials to be supplied described above may be added to the media at once or appropriately during the culture.

The pH of culture media may be appropriately adjusted using a basic compound (e.g., sodium hydroxide, potassium hydroxide, or ammonia) or an acidic compound (e.g., phosphoric acid or sulfuric acid).

Foaming may be adjusted using an antifoaming agent such as fatty acid polyglycol ester. An aerobic condition may be maintained by introducing oxygen or an oxygen-containing gas mixture, for example, air, into a culture medium. Culture temperature may be from 20° C. to 45° C., and specifically, from 25° C. to 40° C. Culturing may be continued until a maximum amount of the desired L-amino acid production is obtained, and specifically from 10 hours to 160 hours. L-arginine may be released into the culture medium or may remain contained in the cell.

Meanwhile, the method of producing L-arginine of the present invention including culturing the microorganism described above may further include a step of recovering L-arginine during the culture. That is, the method of producing L-arginine of the present invention may include culturing a microorganism of the genus *Corynebacterium* in culture media and recovering the L-arginine from the microorganism and the culture media. The step of recovering arginine may mean to separate arginine from cells or culture media using a method of recovering arginine widely known in the art. Methods of recovering L-arginine may include centrifugation, filtration, extraction, spray, drying, evaporation, precipitation, crystallization, electrophoresis, fractional dissolution, chromatography (e.g., ion exchange, affinity, hydrophobicity, size exclusion, and high performance liquid chromatography), etc., but are not limited thereto.

MODE FOR INVENTION

Hereinafter, the present invention will be described in more detail with reference to the following Examples. However, these Examples are for illustrative purposes only, and the invention is not intended to be limited by these Examples.

EXAMPLE 1: CONSTRUCTION OF A VECTOR WITH AN ENHANCED ARGININE OPERON

In order to enhance the arginine operon on the chromosome of a microorganism, a vector where the self-promoter for N-acetylglutamyl phosphate reductase (ArgC) was deleted and substituted with a different promoter was constructed. As the substitution promoter, lysCP1 (SEQ ID NO: 18 disclosed in Korean Patent No. 10-0930203), which has a strong expression-inducing activity, was used.

First, DNA fragments were amplified via primary polymerase chain reaction (PCR) using the chromosomal DNA of a wild type strain of *Corynebacterium glutamicum* (Accession No: ATCC13869) as a template, along with a primer pair of SEQ ID NO: 13 (SF_pargC_PR_pDC infusion primer; 5'-CGAGCTCGGTACCCGGGCAAAGAATACG-GCTTCCTTGGC-3') and SEQ ID NO: 14 (SR_pargC_PR_XbaI-XhoI-BamHI infusion/restriction enzyme primer; 5'-CTGGATCCTCGAGTCTAGAGACGGGTTAGACAT-GCAAAA-3') and a primer pair of SEQ ID NO: 15 (SF_pargC_PR_SpeI-ScaI-BamHI infusion/restriction enzyme primer; 5'-GACTCGAGGATCCAGTACTAGTATGATA-ATCAAGGTTGCAAT-3') and SEQ ID NO: 16 (SR_pargC_PRpDC infusion primer; 5'-TGCAGGTCGACTCTAGGG-TAACGCCTTCTTTCAAAG-3'). The specific conditions for PCR reaction were as follows: the PCR reaction was performed by denaturing at 95° C. for 10 minutes, annealing at 55° C. for 30 seconds, and elongation at 72° C. for 1 minute using a PCR device (Bio-rad C1000 thermal cycler) and Pfu polymerase (Macrogen), and repeated for 28 cycles.

The thus-obtained primary PCR fragments were purified using fragment DNA purification kit (GeneAll), and then three DNA fragments were connected by mixing them with a pD vector, which was already prepared by digesting with XmaI-XbaI restriction enzymes. The connected DNA fragments were subjected to a reaction at 50° C. for 10 minutes using the In-fusion Cloning Kit (Clontech), and thereby a pD-RargC_PR vector was constructed.

The insertion of the substituting promoter was performed in such a manner that lysCP1 promoter was amplified using the pDZ-lysCP1 (Korean Patent No. 10-0930203) as a template along with a primer pair of SEQ ID NO: 5 (SF PlysCP1_XhoI-XbaI infusion primer; 5'-CCGTCTCTA-GACTCGAGCCATCTTTTGGGGTGCGG-3') and SEQ ID NO: 6 (SR_PlysCP1_SpeI infusion primer; 5'-TTGATTAT-CATACTAGTCTTTGTGCACCTTTCGAT-3'), and connected by mixing them with a pD-PargC_PR vector, which was already prepared by digesting with XhoI-SpeI restriction enzymes. The methods of PCR and In-fusion Cloning are the same as described above, and finally a pD-PargC::lysCP1 vector was constructed through the methods.

EXAMPLE 2: CONSTRUCTION OF A VECTOR WITH ENHANCED ORNITHINE CARBAMOYLTRANSFERASE

In order to enhance ornithine carbamoyltransferase, one of arginine biosynthesis enzymes, a recombinant expression vector was constructed. The p117-cj7-GFP (Korean Patent No. 10-0620092) was used as the template vector, and the nucleotide sequence encoding GFP in the template vector was removed by treating with EcoRV-Xba I restriction enzymes, and inserted with argF, derived from a wild type strain of *Corynebacterium glutamicum* ATCC13869, and argF2 (Korean Patent No. 10-0830290).

The DNA fragments of the argF gene were amplified via PCR using the chromosomal DNA of a wild type strain of *Corynebacterium glutamicum* (Accession No: ATCC13869) as a template, along with a primer pair of SEQ ID NO: 7 (SF_argF_EcoRV infusion primer; 5'-ACGAAAGG-AAACACTCGATATCATGACTTCACAACCACAGGT-3') and SEQ ID NO: 8 (SR_argF_XbaI infusion primer; 5'-GCCAAAACAGCTCTAGATTACCTCGGCTGGTG G-GCCA-3'). PCR reaction was performed by denaturing at 95° C. for 10 minutes, annealing at 55° C. for 30 seconds, and elongation at 72° C. for 2 minutes using Pfu polymerase, and repeated for 28 cycles. The thus-obtained PCR fragments were purified and mixed with p117-cj7-GFP, which was already treated with EcoRV-XbaI restriction enzymes, and connected by the In-fusion Cloning method, and thereby a recombinant expression vector, p117-Pcj7-argF, was constructed.

The argF2 gene was amplified via PCR using the chromosomal DNA of a wild type strain of *Corynebacterium glutamicum* (Accession No: ATCC13032) as a template, along with a primer pair of SEQ ID NO: 9 (SF_argF2_EcoRV infusion primer; 5'-ACGAAAGGAAACACTCGA-TATCATGGCCAGAAAACATCTGCT-3') and SEQ ID NO: 10 (SR_argF2_XbaI infusion primer; 5'-GC-CAAAACAGCTCTAGACTACGCATTGATCGACCGA-G-3') and Pfu polymerase (Macrogen), via PCR by denaturing at 95° C. for 10 minutes, annealing at 55° C. for 30 seconds, and elongation at 72° C. for 2 minutes using Pfu polymerase, which was repeated for 28 cycles. The thus-obtained PCR fragments were purified and mixed with p117-cj7-GFP, which was already treated with EcoRV-XbaI restriction enzymes, and connected by the In-fusion Cloning kit, and thereby a recombinant expression vector, p117-Pcj7-argF2, was constructed.

Additionally, a recombinant expression vector, which can simultaneously express both argF and argF2 genes, was constructed. The thus-constructed expression vector, p117-Pcj7-argF, was treated with NotI and then p117-Pcj7-argF2 was inserted thereinto. Specifically, PCR reaction was performed using the recombinant plasmid, p117-Pcj7-argF2, as a template, along with SEQ ID NO: 11 (SF_Pcj7_argF2_NotI infusion primer; 5'CCTTTTTGCGGCGGC-CGCAGAAACATCCCAGCGCTACT-3') and SEQ ID NO: 12 (SR_argF2_NotI infusion primer; 5'-CACCGCGGTG-GCGGCCGCCGCAAAAAGGCCATCCGTCA-3') primer and Pfu polymerase, by denaturing at 95° C. for 10 minutes, annealing at 55° C. for 30 seconds, and elongation at 72° C. for 2.5 minutes, and was repeated for 28 cycles. The thus-obtained PCR fragments were purified and mixed with p117-Pcj7-argF, which was already treated with NotI restriction enzyme, and connected by the In-fusion Cloning kit, and finally a recombinant expression vector, p117-Pcj7-argF/Pcj7-argF2, was constructed.

EXAMPLE 3: CONSTRUCTION OF A STRAIN HAVING A RECOMBINANT VECTOR INSERTED THEREIN

3-1. Insertion of a Vector With an Enhanced Arginine Operon

In order to substitute a self-promoter of an arginine operon on the chromosome of *Corynebacterium*, pD-PargC::lysCP1, the recombinant vector constructed in Example 1, was transformed into an existing arginine-producing *Corynebacterium* strain, and thereby a *Corynebacterium* strain inserted with a recombinant vector was constructed. Specifically, lysCP1 promoter sequence was inserted into the chromosome by transforming pD-PargC::lysCP1, the recombinant vector constructed in Example 1, into the existing arginine-producing strains of KCCM10741P (Korean Patent No. 10-07916590) and ATCC21831, thereby substituting the self-promoter sequence possessed by the parental strain with the promoter sequence of the vector via homologous recombination.

In performing the transformation, the recombinant vector was first inserted into KCCM10741P and ATCC21831 via an electric pulse method (Appl Microbiol Biotechnol. 1999 October; 52(4): 541-5), and the strains with the insertions on their chromosome by the recombination of homologous sequences were selected in media containing 25 mg/L kanamycin. The selected primary strains were subjected to cross-over, and thereby those strains, where the promoters were substituted with lysCP1 promoter and the vector was removed, were selected. The presence of promoter substitution in the final transformed strains was confirmed by PCR using a primer pair of SEQ ID NO: 5 and SEQ ID NO: 6, and the strains were named as KCCM10741P_ΔPargC::lysCP1 and ATCC21831_ΔPargC::lysCP1.

3-2. Insertion of a Vector With Enhanced Ornithine Carbamoyltransferase

The recombinant expression vectors, p117-Pcj7-argF, p117-Pcj7-argF2, and p117-Pcj7-argF/Pcj7-argF2 constructed in Example 2, was inserted into the strain KCCM10741P_ΔPargC::lysCP1 and ATCC21831_ ΔPargC::lysCP1 by electric pulse method, selected in media containing 25 mg/L kanamycin, and the strains further expressing argF, argF2, and argF/argF2 were finally constructed. The strains were named as KCCM10741P_ ΔPargC::lysCP1_Pcj7-argF, KCCM10741P_ΔPargC:: lysCP1_Pcj7-argF2, KCCM10741P_ΔPargC::lysCP1_Pcj7-argF/Pcj7-argF2, ATCC21831_ΔPargC::lysCP1_Pcj7-argF, ATCC21831_ΔPargC::lysCP1_Pcj7-argF2, and ATCC-21831_ΔPargC::lysCP1_Pcj7-argF/Pcj7-argF2, and among them, KCCM10741P_ΔPargC::lysCP1_Pcj7-argF2 was renamed as CA06-2044, and deposited at Korean Culture Center of Microorganisms (KCCM) under the Budapest Treaty on Dec. 9, 2013 under the accession number KCCM11498P.

EXAMPLE 4: EVALUATION OF CONSTRUCTED STRAINS

In order to examine the effect of enhancement of the arginine operon and ornithine carbamoyltransferase on arginine-producing ability using *Corynebacterium glutamicum* KCCM10741P_ΔPargC::lysCP1, KCCM10741P_ΔPargC:: lysCP1_Pcj7-argF, KCCM10741P_ΔPargC::lysCP1_Pcj7-argF2, KCCM10741P_ΔPargC::lysCP1_Pcj7-argF/Pcj7-argF2, ATCC21831_ΔPargC::lysCP1, ATCC21831_ ΔPargC::lysCP1_Pcj7-argF, ATCC21831_ΔPargC::lysCP1_ Pcj7-argF2, and ATCC21831_ΔPargC::lysCP1_Pcj7-argF/ Pcj7-argF2, which are arginine-producing strains constructed in Example 3, they were cultured as shown below. In particular, *Corynebacterium glutamicum* KCCM10741P and ATCC21831, which are the parental strains, were used as control, and a platinum loop of the strains was respectively inoculated onto a 250 mL corner-baffled flask containing 25 mL (6% glucose, 3% ammonium sulfate, 0.1% potassium phosphate, 0.2% magnesium sulfate heptahydrate, 1.5% corn steep liquor (CSL), 1% NaCl, 0.5% yeast extract, and 100 μg/L biotin, pH 7.2) of a production medium, and incubated at 30° C. at 200 rpm for 48 hours. Upon completion of culturing, the amount of L-arginine production was measured by HPLC, and the results are shown in Table 1 below.

TABLE 1

Confirmation of arginine-producing abilities by parent strain and recombinant strains

| Strain | OD | Conc. of arginine (g/L) | Conc. of ornithine (g/L) |
| --- | --- | --- | --- |
| KCCM10741P | 91 | 3.0 | 0.2 |
| KCCM10741P_ΔPargC::lysCP1 | 72 | 2.2 | 1.9 |
| KCCM10741P_ΔPargC::lysCP1_Pcj7-argF | 69 | 4.3 | 0.2 |
| KCCM10741P_ΔPargC::lysCP1_Pcj7-argF2 | 70 | 4.1 | 0.5 |
| KCCM10741P_ΔPargC::lysCP1_Pcj7-argF/Pcj7-argF2 | 69 | 4.5 | 0.2 |
| ATCC21831 | 102 | 4.2 | 0.3 |
| ATCC21831_ΔPargC::1ysCP1 | 86 | 3.2 | 2.9 |
| ATCC21831_ΔPargC::lysCP1_Pcj7-argF | 86 | 5.5 | 0.3 |
| ATCC21831_ΔPargC::lysCP1_Pcj7-argF2 | 88 | 5.3 | 0.6 |
| ATCC21831_ΔPargC::lysCP1_Pcj7-argF/Pcj7-argF2 | 85 | 5.6 | 0.3 |

As shown in Table 1 above, the strains, where the genes encoding arginine operon and ornithine carbamoyltransferase were simultaneously enhanced, showed a maximum of 50% increase in arginine-producing ability compared to that of control. Additionally, the increases in arginine concentration and ornithine concentration, shown in the enhancement of the arginine operon alone (KCCM-10741P_ΔPargC::lysCP1 and ATCC21831_ΔPargC::lysCP1), were solved by introducing argF, argF2 or argF and argF2, and eventually showing the result of increase in arginine concentration.

From the foregoing, one of ordinary skill in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A modified *Corynebacterium glutamicum* microorganism having an ability to produce L-arginine, wherein the modified *Corynebacterium glutamicum* comprises an arginine operon comprising genes encoding N-acetylglutamyl phosphate reductase, glutamate N-acetyltransferase, N-acetylglutamate kinase, acetylornithine aminotransferase, ornithine carbamoyltransferase, and arginine repressor, wherein the native promoter of the arginine operon is replaced with a stronger promoter and wherein the expression of all of the genes encoding the N-acetylglutamyl phosphate reductase, glutamate N-acetyltransferase, N-acetylglutamate kinase, acetylornithine aminotransferase, ornithine carbamoyltransferase, and arginine repressor is enhanced in the modified *Corynebacterium glutamicum* as compared to a wild-type *Corynebacterium glutamicum*, and wherein the modified *Corynebacterium glutamicum* microorganism comprises at least one additional copy of a gene encoding ornithine carbamoyltransferase by transformation with a vector comprising a gene encoding ornithine carbamoyltransferase, by inserting an additional gene encoding ornithine carbamoyltransferase into the chromosome, and a combination thereof, and wherein the expression of the at least one additional copy of the gene encoding ornithine carbamoyltransferase is enhanced in the modified *Corynebacterium glutamicum* as compared to a *Corynebacterium glutamicum* without the at least one additional copy.

2. The modified *Corynebacterium glutamicum* microorganism of claim 1, wherein the ornithine carbamoyltransferase comprises the amino acid sequence of SEQ ID NO: 1 or SEQ ID NO: 3.

3. A method of producing L-arginine, comprising:

culturing the modified *Corynebacterium glutamicum* microorganism of claim 1 or claim 2 in a culture media; and recovering the L-arginine from the microorganism or the media.

* * * * *

SEQUENCE LISTING

```
<160> NUMBER OF SEQ ID NOS: 26

<210> SEQ ID NO 1
<211> LENGTH: 319
<212> TYPE: PRT
<213> ORGANISM: Corynebacterium glutamicum
<220> FEATURE:
<221> NAME/KEY: MISC_FEATURE
<222> LOCATION: (1)..(319)
<223> OTHER INFORMATION: ornithine carbamoyltransferase (ArgF)

<400> SEQUENCE: 1

Met Thr Ser Gln Pro Gln Val Arg His Phe Leu Ala Asp Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80

Ser Gln Met Gly Lys Gly Glu Thr Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala His Gln Pro Arg
305                 310                 315


<210> SEQ ID NO 2
<211> LENGTH: 960
<212> TYPE: DNA
<213> ORGANISM: Corynebacterium glutamicum
```

-continued

<220> FEATURE:
<221> NAME/KEY: misc_feature
<222> LOCATION: (1)..(957)
<223> OTHER INFORMATION: ornithine carbamoyltransferase (ArgF)

<400> SEQUENCE: 2

```
atgacttcac aaccacaggt tcgccatttc ctggctgatg atgatctcac ccctgcagag      60

caggcagagg ttttgaccct agccgcaaag ctcaaggcag cgccgttttc ggagcgtcca     120

ctcgagggac caaagtccgt tgcagttctt tttgataaga cttcaactcg tactcgcttc     180

tccttcgacg cgggcatcgc tcatttgggt ggacatgcca tcgtcgtgga ttccggcagc     240

tcacagatgg gtaagggcga gaccctgcag gacaccgcag ctgtattgtc ccgctacgtg     300

gaagcaattg tgtggcgcac ctacgcacac agcaatttcc acgccatggc ggagacgtcc     360

actgtgccac tggtgaactc cttgtccgat gatctgcacc catgccagat tctggctgat     420

ctgcagacca tcgtggaaaa cctcagccct gaagaaggcc cagcaggcct taagggtaag     480

aaggctgtgt acctgggcga tggcgacaac aacatggcca actcctacat gattggcttt     540

gccaccgcgg gcatggatat ctccatcatc gctcctgaag ggttccagcc tcgtgcggaa     600

ttcgtggagc gcgcggaaaa gcgtggccag gaaaccggcg cgaaggttgt tgtcaccgac     660

agcctcgacg aggttgccgg cgccgatgtt gtcatcaccg atacctgggt atccatgggt     720

atggaaaacg acggcatcga tcgcaccaca cctttcgttc cctaccaggt caacgatgag     780

gtcatggcga aagctaacga cggcgccatc ttcctgcact gccttcctgc ctaccgcggc     840

aaagaagtgg cagcctccgt gattgatgga ccagcgtcca aagttttcga tgaagcagaa     900

aaccgcctcc acgctcagaa agcactgctg gtgtggctgc tggcccacca gccgaggtaa     960
```

<210> SEQ ID NO 3
<211> LENGTH: 274
<212> TYPE: PRT
<213> ORGANISM: Corynebacterium glutamicum
<220> FEATURE:
<221> NAME/KEY: MISC_FEATURE
<222> LOCATION: (1)..(274)
<223> OTHER INFORMATION: ornithine carbamoyltransferase (ArgF2)

<400> SEQUENCE: 3

```
Met Ala Arg Lys His Leu Leu Ser Leu Ala Asp Trp Asn Arg Gly Glu
1               5                   10                  15

Leu Glu Ala Leu Phe Glu Leu Ala Glu Gln Tyr Glu Ala Gly Gly Gly
            20                  25                  30

Pro Arg Phe Asp Gly Ala Ala Ala Met Phe Phe Pro Pro Thr Ser Leu
        35                  40                  45

Arg Thr Arg Leu Ser Phe Glu Arg Gly Ala Thr Ala Met Gly Leu Gln
    50                  55                  60

Pro Ile Thr Phe Pro Ser Asp Ser Leu Asp Lys Asp Glu Asp Leu Val
65                  70                  75                  80

Asp Val Val Gly Tyr Leu Ser Gln Trp Ala Asp Val Val Val Val Arg
                85                  90                  95

His Pro Gln Leu Thr Ala Leu Gln Arg Leu Ala Ser Ala Asp Ala Ala
            100                 105                 110

Pro Val Ile Asn Ala Met Thr Ser Glu Asn His Pro Cys Glu Val Leu
        115                 120                 125

Ser Asp Leu Tyr Ala Leu Ser Arg His His Asp Ile Ser Ala Leu Arg
    130                 135                 140

Tyr Leu Phe Val Gly Gly Asp Gly Asn Ile Ala Arg Ala Trp Trp Glu
```

-continued

```
145                 150                 155                 160

Ala Ala Gln Ala Phe Gly Leu Glu Met Arg Gln Ser Cys Pro Glu Glu
                165                 170                 175

Leu Arg Val Val Gly Met Pro Trp Glu Glu Asn Leu Pro His Ala Ile
            180                 185                 190

Ala Ser Ala Asp Val Val Leu Thr Asp Gly Pro Gly Arg His Ala Glu
        195                 200                 205

Leu Leu Glu Pro Tyr Arg Val Thr Ala Ala Leu Leu Asp Arg Ala Pro
    210                 215                 220

Arg Gly Val Arg Leu Ala Pro Cys Pro Pro Phe Ile Arg Gly Arg Glu
225                 230                 235                 240

Val Ser Ala Asp Ala Ile Glu His Pro Ala Phe Val Gly Tyr Ser Phe
                245                 250                 255

Lys Arg His Leu Met Pro Val Gln Gln Ala Ile Leu Ala Arg Ser Ile
            260                 265                 270

Asn Ala


<210> SEQ ID NO 4
<211> LENGTH: 825
<212> TYPE: DNA
<213> ORGANISM: Corynebacterium glutamicum
<220> FEATURE:
<221> NAME/KEY: misc_feature
<222> LOCATION: (1)..(822)
<223> OTHER INFORMATION: ornithine carbamoyltransferase (ArgF2)

<400> SEQUENCE: 4

atggccagaa aacatctgct ctccctggca gactggaaca gaggcgagct tgaggcatta      60

ttcgagctcg cggagcagta tgaagctggc ggtgggccac gattcgatgg tgccgcggcg     120

atgttcttcc cgccgacgag tttgcgtaca cggctctcat tcgagcgtgg ggcaacggca     180

atgggactcc agccgatcac gttcccgtca gacagcctgg acaaggacga agatctcgtc     240

gacgtcgtcg gctatctctc gcagtgggct gatgtcgttg tcgtccgaca cccgcaattg     300

acggcgcttc agcggttggc gtcagcggat gcagcgcccg tgatcaacgc gatgacgagt     360

gagaaccatc cgtgcgaagt cctctcggac ttgtatgcgc tgtctcgtca ccatgacatt     420

tcggccctgc ggtacctgtt tgtcggtggc gatggcaaca tcgccagggc ctggtgggag     480

gcggcccaag cgttcggcct cgagatgcgg cagagttgtc ctgaagagct gcgtgtcgtc     540

gggatgccgt gggaggagaa cctgccgcat gcaattgcat cagcggatgt cgtgctgacg     600

gatgggccag gtagacatgc ggagttactc gagccgtatc gtgtgaccgc tgcgttgttg     660

gatcgcgcgc cccgtggagt gcggctcgcg ccctgcccgc cgttcatccg cgggcgcgaa     720

gtgagcgccg atgcgatcga gcatccggcg ttcgtcgggt actcgttcaa gcgtcatctc     780

atgccggttc agcaggcgat tctggctcgg tcgatcaatg cgtag                     825


<210> SEQ ID NO 5
<211> LENGTH: 35
<212> TYPE: DNA
<213> ORGANISM: Artificial Sequence
<220> FEATURE:
<223> OTHER INFORMATION: SF_PlysCP1_XhoI-XbaI primer

<400> SEQUENCE: 5

ccgtctctag actcgagcca tcttttgggg tgcgg                                 35


<210> SEQ ID NO 6
```

-continued

<211> LENGTH: 35
<212> TYPE: DNA
<213> ORGANISM: Artificial Sequence
<220> FEATURE:
<223> OTHER INFORMATION: SR_PlysCP1_SpeI primer

<400> SEQUENCE: 6
ttgattatca tactagtctt tgtgcacctt tcgat 35

<210> SEQ ID NO 7
<211> LENGTH: 42
<212> TYPE: DNA
<213> ORGANISM: Artificial Sequence
<220> FEATURE:
<223> OTHER INFORMATION: SF_argF_EcoRV primer

<400> SEQUENCE: 7
acgaaaggaa acactcgata tcatgacttc acaaccacag gt 42

<210> SEQ ID NO 8
<211> LENGTH: 37
<212> TYPE: DNA
<213> ORGANISM: Artificial Sequence
<220> FEATURE:
<223> OTHER INFORMATION: SR_argF_XbaI primer

<400> SEQUENCE: 8
gccaaaacag ctctagatta cctcggctgg tgggcca 37

<210> SEQ ID NO 9
<211> LENGTH: 42
<212> TYPE: DNA
<213> ORGANISM: Artificial Sequence
<220> FEATURE:
<223> OTHER INFORMATION: SF_argF2_EcoRV primer

<400> SEQUENCE: 9
acgaaaggaa acactcgata tcatggccag aaaacatctg ct 42

<210> SEQ ID NO 10
<211> LENGTH: 37
<212> TYPE: DNA
<213> ORGANISM: Artificial Sequence
<220> FEATURE:
<223> OTHER INFORMATION: SR_argF2_XbaI primer

<400> SEQUENCE: 10
gccaaaacag ctctagacta cgcattgatc gaccgag 37

<210> SEQ ID NO 11
<211> LENGTH: 38
<212> TYPE: DNA
<213> ORGANISM: Artificial Sequence
<220> FEATURE:
<223> OTHER INFORMATION: SF_Pcj7_argF2_NotI primer

<400> SEQUENCE: 11
cctttttgcg gcggccgcag aaacatccca gcgctact 38

<210> SEQ ID NO 12
<211> LENGTH: 38
<212> TYPE: DNA
<213> ORGANISM: Artificial Sequence
<220> FEATURE:
<223> OTHER INFORMATION: SR_argF2_NotI primer

<400> SEQUENCE: 12
caccgcggtg gcggccgccg caaaaaggcc atccgtca 38

<210> SEQ ID NO 13
<211> LENGTH: 39
<212> TYPE: DNA
<213> ORGANISM: Artificial Sequence
<220> FEATURE:
<223> OTHER INFORMATION: SF_pargC_PR_pDC primer

<400> SEQUENCE: 13
cgagctcggt acccgggcaa agaatacggc ttccttggc 39

<210> SEQ ID NO 14
<211> LENGTH: 39
<212> TYPE: DNA
<213> ORGANISM: Artificial Sequence
<220> FEATURE:
<223> OTHER INFORMATION: SR_pargC_PR_XbaI-XhoI-BamHI primer

<400> SEQUENCE: 14
ctggatcctc gagtctagag acgggttaga catgcaaaa 39

<210> SEQ ID NO 15
<211> LENGTH: 42
<212> TYPE: DNA
<213> ORGANISM: Artificial Sequence
<220> FEATURE:
<223> OTHER INFORMATION: SF_pargC_PR_SpeI-ScaI-BamHI primer

<400> SEQUENCE: 15
gactcgagga tccagtacta gtatgataat caaggttgca at 42

<210> SEQ ID NO 16
<211> LENGTH: 36
<212> TYPE: DNA
<213> ORGANISM: Artificial Sequence
<220> FEATURE:
<223> OTHER INFORMATION: SR_pargC_PR_pDC primer

<400> SEQUENCE: 16
tgcaggtcga ctctagggta acgccttctt tcaaag 36

<210> SEQ ID NO 17
<211> LENGTH: 317
<212> TYPE: DNA
<213> ORGANISM: Artificial Sequence
<220> FEATURE:
<223> OTHER INFORMATION: Corynebacterium glutamicum modified
heterogeneous cj7 promoter

<400> SEQUENCE: 17
agaaacatcc cagcgctact aatagggagc gttgaccttc cttccacgga ccggtaatcg 60
gagtgcctaa aaccgcatgc ggcttaggct ccaagatagg ttctgcgcgg ccgggtaatg 120
catcttcttt agcaacaagt tgaggggtag gtgcaaataa gaacgacata gaaatcgtct 180
cctttctgtt tttaatcaac atacaccacc acctaaaaat tccccgacca gcaagttcac 240
agtattcggg cacaatatcg ttgccaaaat attgtttcgg aatatcatgg gatacgtacc 300
caacgaaagg aaacact 317

<210> SEQ ID NO 18
<211> LENGTH: 353
<212> TYPE: DNA
<213> ORGANISM: Artificial Sequence -continued
<220> FEATURE:
<223> OTHER INFORMATION: Corynebacterium glutamicum modified
heterogeneous lysCP1 promoter

<400> SEQUENCE: 18

```
ccatcttttg gggtgcggag cgcgatccgg tgtctgacca cggtgcccca tgcgattgtt     60

aatgccgatg ctagggcgaa aagcacggcg agcagattgc tttgcacttg attcagggta    120

gttgactaaa gagttgctcg cgaagtagca cctgtcactt ttgtctcaaa tattaaatcg    180

aatatcaata tatggtctgt ttattggaac gcgtcccagt ggctgagacg catccgctaa    240

agccccagga accctgtgca gaaagaaaac actcctctgg ctaggtagac acagtttatt    300

gtggtagagt tgagcgggta actgtcagca cgtagatcga aaggtgcaca aag           353
```

<210> SEQ ID NO 19
<211> LENGTH: 388
<212> TYPE: PRT
<213> ORGANISM: Corynebacterium glutamicum
<220> FEATURE:
<221> NAME/KEY: MISC_FEATURE
<222> LOCATION: (1)..(388)
<223> OTHER INFORMATION: glutamate N-acetyltransferase (ArgJ)

<400> SEQUENCE: 19

```
Met Ala Lys Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Ala Val Phe Thr Arg Asn
        35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Thr Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
```

-continued

```
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Asp Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385
```

<210> SEQ ID NO 20
<211> LENGTH: 1167
<212> TYPE: DNA
<213> ORGANISM: Corynebacterium glutamicum
<220> FEATURE:
<221> NAME/KEY: misc_feature
<222> LOCATION: (1)..(1164)
<223> OTHER INFORMATION: glutamate N-acetyltransferase (ArgJ)

<400> SEQUENCE: 20

```
atggccaaaa aaggcattac cgcgccgaaa ggcttcgttg cttctgcaac gaccgcgggt      60

attaaagctt ctggcaatcc tgacatggcg ttggtggtta accagggtcc agagttttcc     120

gcagcggccg tgtttacacg caaccgagtt ttcgcagcgc ctgtgaaggt gagccgggag     180

aacgttgctg atggccagat cagggctgtt ttgtacaacg ctggtaatgc taatgcgtgt     240

aatggtctgc agggtgagaa ggatgctcgt gagtctgttt ctcatctagc tcaaaatttg     300

ggcttggagg attccgatat tggtgtgtgt tccactggtc ttattggtga gttgcttccg     360

atggataagc tcaatacagg tattgatcag ctgaccgctg agggcgcttt gggtgacaat     420

ggtgcagctg ctgccaaggc gatcatgacc actgacacgg tggataagga aaccgtcgtg     480

tttgctgatg gttggactgt cggcggaatg ggcaagggcg tgggcatgat ggcgccgtct     540

cttgccacca tgctggtctg cttgaccact gatgcatccg ttactcagga aatggctcag     600

attgcgctgg ctaatgctac ggccgttacg tttgacaccc tggatattga tggatcaacc     660

tccaccaatg acaccgtgtt cctgctggca tctggcgcta gcggaatcac cccaactcag     720

gatgaactca acgatgcggt gtacgcagct tgttctgata tcgcagcgaa gcttcaggct     780

gatgcagagg gggtgaccaa gcgcgttgct gtgacagtgg tgggaaccac caacaacgag     840

caggcgatca atgcggctcg cacggttgct cgtgacaatt tgttcaagtg cgcaatgttt     900

ggatctgatc caaactgggg tcgcgtgttg gctgcagtcg gcatggctga tgctgatatg     960

gaaccagaga agatttctgt gttcttcaat gatcaagcag tatgccttga ttccactggc    1020

gctcctggtg ctcgtgaggt ggatctttcc ggcgctgaca ttgatgtccg aattgatttg    1080

ggcaccagtg gggaaggcca ggcaacagtt cgaaccactg acctgagctt ctcctacgtg    1140

gagatcaact ccgcgtacag ctcttaa                                        1167
```

-continued

<210> SEQ ID NO 21
<211> LENGTH: 317
<212> TYPE: PRT
<213> ORGANISM: Corynebacterium glutamicum
<220> FEATURE:
<221> NAME/KEY: MISC_FEATURE
<222> LOCATION: (1)..(317)
<223> OTHER INFORMATION: N-acetylglutamate kinase (ArgB)

<400> SEQUENCE: 21

```
Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315
```

<210> SEQ ID NO 22
<211> LENGTH: 954
<212> TYPE: DNA
<213> ORGANISM: Corynebacterium glutamicum
<220> FEATURE:
<221> NAME/KEY: misc_feature
<222> LOCATION: (1)..(951)

-continued

<223> OTHER INFORMATION: N-acetylglutamate kinase (ArgB)

<400> SEQUENCE: 22
atgaatgact tgatcaaaga tttaggctct gaggtgcgcg caaatgtcct cgctgaggcg 60
ttgccatggt tgcagcattt ccgcgacaag attgttgtcg tgaaatatgg cggaaacgcc 120
atggtggatg atgatctcaa ggctgctttt gctgccgaca tggtcttctt gcgcaccgtg 180
ggcgcaaaac cagtggtggt gcacggtggt ggacctcaga tttctgagat gctaaaccgt 240
gtgggtctcc agggcgagtt caagggtggt ttccgtgtga ccactcctga ggtcatggac 300
attgtgcgca tggtgctctt tggtcaggtc ggtcgcgatt tagttggttt gatcaactct 360
catggccctt acgctgtggg aacctccggt gaggatgccg gcctgtttac cgcgcagaag 420
cgcatggtca acatcgatgg cgtacccact gatattggtt tggtcggaga catcattaat 480
gtcgatgcct cttccttgat ggatatcatc gaggccggtc gcattcctgt ggtctctacg 540
attgctccag gcgaagacgg ccagatttac aacatcaacg ccgataccgc agcgggtgct 600
ttggctgcag cgattggtgc agaacgcctg ctggttctca ccaatgtgga aggtctgtac 660
accgattggc ctgataagag ctcactggtg tccaagatca aggccaccga gctggaggcc 720
attcttccgg gacttgattc cggcatgatt ccaaagatgg agtcttgctt gaatgcggtg 780
cgtgggggag taagcgctgc tcatgtcatt gacggccgca tcgcgcactc ggtgttgctg 840
gagcttttga ccatgggtgg aattggcacg atggtgctgc cggatgtttt tgatcgggag 900
aattatccgg aaggcaccgt ttttagaaaa gacgacaagg atggggaact gtaa 954

<210> SEQ ID NO 23
<211> LENGTH: 347
<212> TYPE: PRT
<213> ORGANISM: Corynebacterium glutamicum
<220> FEATURE:
<221> NAME/KEY: MISC_FEATURE
<222> LOCATION: (1)..(347)
<223> OTHER INFORMATION: N-acetylglutamyl phosphate reductase (ArgC)

<400> SEQUENCE: 23

Met Thr Ile Lys Val Ala Ile Ala Gly Ala Ser Gly Tyr Ala Gly Gly
1 5 10 15

Glu Ile Leu Arg Leu Leu Leu Gly His Pro Ala Tyr Ala Ser Gly Glu
20 25 30

Leu Glu Ile Gly Ala Leu Thr Ala Ala Ser Thr Ala Gly Ser Thr Leu
35 40 45

Gly Glu Leu Met Pro His Ile Pro Gln Leu Ala Asp Arg Val Ile Gln
50 55 60

Asp Thr Thr Ala Glu Thr Leu Ala Gly His Asp Val Val Phe Leu Gly
65 70 75 80

Leu Pro His Gly Phe Ser Ala Glu Ile Ala Leu Gln Leu Gly Pro Asp
85 90 95

Val Thr Val Ile Asp Cys Ala Ala Asp Phe Arg Leu Gln Asn Ala Ala
100 105 110

Asp Trp Glu Lys Phe Tyr Gly Ser Glu His Gln Gly Thr Trp Pro Tyr
115 120 125

Gly Ile Pro Glu Ile Pro Gly His Arg Glu Ala Leu Arg Gly Ala Lys
130 135 140

Arg Val Ala Val Pro Gly Cys Phe Pro Thr Gly Ala Thr Leu Ala Leu
145 150 155 160

Leu Pro Ala Val Gln Ala Gly Leu Ile Glu Pro Asp Val Ser Val Val

-continued

```
                165                 170                 175

Ser Ile Thr Gly Val Ser Gly Ala Gly Lys Lys Ala Ser Val Ala Leu
            180                 185                 190

Leu Gly Ser Glu Thr Met Gly Ser Leu Lys Ala Tyr Asn Thr Ser Gly
        195                 200                 205

Lys His Arg His Thr Pro Glu Ile Ala Gln Asn Leu Gly Glu Val Ser
    210                 215                 220

Asp Lys Pro Val Lys Val Ser Phe Thr Pro Val Leu Ala Pro Leu Pro
225                 230                 235                 240

Arg Gly Ile Leu Thr Thr Ala Thr Ala Pro Leu Lys Glu Gly Val Thr
                245                 250                 255

Ala Glu Gln Ala Arg Ala Val Tyr Glu Glu Phe Tyr Ala Gln Glu Thr
            260                 265                 270

Phe Val His Val Leu Pro Glu Gly Ala Gln Pro Gln Thr Gln Ala Val
        275                 280                 285

Leu Gly Ser Asn Met Cys His Val Gln Val Glu Ile Asp Glu Glu Ala
    290                 295                 300

Gly Lys Val Leu Val Thr Ser Ala Ile Asp Asn Leu Thr Lys Gly Thr
305                 310                 315                 320

Ala Gly Ala Ala Val Gln Cys Met Asn Leu Ser Val Gly Phe Asp Glu
                325                 330                 335

Ala Ala Gly Leu Pro Gln Val Gly Val Ala Pro
            340                 345
```

<210> SEQ ID NO 24
<211> LENGTH: 1044
<212> TYPE: DNA
<213> ORGANISM: Corynebacterium glutamicum
<220> FEATURE:
<221> NAME/KEY: misc_feature
<222> LOCATION: (1)..(1041)
<223> OTHER INFORMATION: N-acetylglutamyl phosphate reductase (ArgC)

<400> SEQUENCE: 24

```
atgacaatca aggttgcaat cgcaggagcc agtggatatg ccggcggaga aatccttcgt      60

ctccttttag gccatccagc ttatgcatct ggtgaactag aaatcggagc actcaccgcg     120

gcatcaaccg caggcagcac gctcggtgaa ttgatgccac acattccgca gttggcggat     180

cgtgttattc aagacaccac agctgaaact ctagccggtc atgatgtcgt atttctagga     240

cttccacacg gattctctgc agaaattgca cttcagctcg gaccagatgt cacagtgatt     300

gactgtgcag ctgactttcg tctgcaaaat gctgcagatt gggagaagtt ctacggctca     360

gagcaccagg gaacatggcc ttatggcatt ccagaaatac caggacaccg cgaggctctt     420

cgtggtgcta agcgtgtagc agtgccagga tgtttcccaa ccggtgcaac cttggctctt     480

cttcctgcgg ttcaagcggg acttatcgag ccagatgttt ccgtagtgtc catcaccggc     540

gtatcaggtg caggtaagaa agcatctgtt gcactacttg gctcggaaac catgggttca     600

ctcaaggcgt acaacacctc cggaaagcac cgccacaccc cggaaattgc ccagaacctc     660

ggcgaagtca gcgacaagcc agtcaaggtg agcttcaccc cagtgcttgc accgttacct     720

cgcggaattc tcaccactgc aaccgcacct ttgaaagaag gcgttaccgc agagcaggct     780

cgcgcagtat atgaagagtt ctatgcacag gaaaccttcg tgcatgttct tccagaaggt     840

gcacagccac aaacccaagc agttcttggc tccaacatgt gccacgtgca ggtagaaatt     900

gatgaggaag caggcaaagt ccttgttacc tccgcaatcg ataacctcac caagggaact     960
```

-continued

```
gccggcgccg ctgttcagtg catgaactta agcgttggct ttgatgaggc agcaggcctg   1020

ccacaggtcg gcgtcgcacc ttaa                                          1044


<210> SEQ ID NO 25
<211> LENGTH: 391
<212> TYPE: PRT
<213> ORGANISM: Corynebacterium glutamicum
<220> FEATURE:
<221> NAME/KEY: MISC_FEATURE
<222> LOCATION: (1)..(391)
<223> OTHER INFORMATION: acetylornithine aminotransferase (ArgD)

<400> SEQUENCE: 25

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Lys Val Tyr Ile Asp Leu Leu Ala Gly Ile Ala Val Asn
        35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
    290                 295                 300

Cys Ala Glu Val Thr Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335
```

-continued

```
Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
385                 390


<210> SEQ ID NO 26
<211> LENGTH: 1176
<212> TYPE: DNA
<213> ORGANISM: Corynebacterium glutamicum
<220> FEATURE:
<221> NAME/KEY: misc_feature
<222> LOCATION: (1)..(1173)
<223> OTHER INFORMATION: acetylornithine aminotransferase (ArgD)

<400> SEQUENCE: 26

atgagcacgc tggaaacttg gccacaggtc attattaata cgtacggcac cccaccagtt      60

gagctggtgt ccggcaaggg cgcaaccgtc accgatgacc agggcaaagt ctacatcgac     120

ttgctcgcgg gcatcgcagt caacgcgttg ggccacgccc acccggcgat catcgaggcg     180

gtcaccaacc agatcggcca acttggtcac gtctcaaact tgttcgcatc caggcccgtc     240

gtcgaggtcg ccgaggagct catcaagcgt ttttcgcttg acgacgccac cctcgccgcg     300

caaacccggg ttttcttctg caactcgggc gccgaagcaa acgaggctgc tttcaagatt     360

gcacgcttga ctggtcgttc ccggattctg gctgcagttc atggtttcca cggccgcacc     420

atgggttccc tcgcgctgac tggccagcca gacaagcgtg aagcattcct gccaatgcca     480

agcggtgtgg agttctaccc ttacggcgac accgattact tgcgcaaaat ggtagaaacc     540

aacccaacgg atgtggctgc tatcttcctc gagccaatcc agggtgaaac gggcgttgtt     600

ccagcacctg aaggattcct caaggcagtg cgcgagctgt gcgatgagta cggcatcttg     660

atgatcaccg atgaagtcca gactggcgtt ggccgtaccg gcgatttctt tgcacatcag     720

cacgatggcg ttgttcccga tgtggtgacc atggccaagg gacttggcgg cggtcttccc     780

atcggtgctt gtttggccac tggccgtgca gctgaattga tgaccccagg caagcacggc     840

accactttcg gtggcaaccc agttgcttgt gcagctgcca aggcagtgct gtctgttgtc     900

gatgacgctt tctgcgcaga agttacccgc aagggcgagc tgttcaagga acttcttgcc     960

aaggttgacg gcgttgtaga cgtccgtggc aggggcttga tgttgggcgt ggtgctggag    1020

cgcgacgtcg caaagcaagc tgttcttgat ggttttaagc acggcgttat tttgaatgca    1080

ccggcggaca acattatccg tttgaccccg ccgctggtga tcaccgacga agaaatcgca    1140

gacgcagtca aggctattgc cgagacaatc gcataa                              1176
```